United States Patent [19]

Baltes

[11] Patent Number: 4,625,432

[45] Date of Patent: Dec. 2, 1986

[54] APPARATUS AND METHOD FOR DRYING AND STERILIZING FABRICS

[76] Inventor: Hans Baltes, Heideweg 27, D-4600 Dortmund 30, Fed. Rep. of Germany

[21] Appl. No.: 676,578

[22] Filed: Nov. 30, 1984

[30] Foreign Application Priority Data

Nov. 30, 1983 [DE] Fed. Rep. of Germany ....... 3343236

[51] Int. Cl.$^4$ .............................................. F26B 9/06
[52] U.S. Cl. ........................................ 34/151; 34/197; 34/202; 34/86; 34/225; 34/233; 34/196
[58] Field of Search .................. 422/28, 37, 300, 292; 312/236, 136, 326; 211/99, 100; 34/151, 86, 225, 233, 239, 240, 197, 30, 48, 202

[56] References Cited

U.S. PATENT DOCUMENTS

| 354,798 | 12/1886 | Lorimer | 422/28 |
| 3,508,340 | 4/1970 | Kombol | 34/48 |
| 4,180,919 | 1/1980 | Baltes | 34/151 |
| 4,527,343 | 7/1985 | Danneberg | 34/35 |

Primary Examiner—Larry I. Schwartz
Attorney, Agent, or Firm—Felfe & Lynch

[57] ABSTRACT

Apparatus for the drying and sterilizing of fabrics, the apparatus comprising a drier cabinet provided with means for suspending therein fabric articles, and with means for generating, distributing and circulating warm air for drying purposes and hot air for the sterilization of the fabric articles.

10 Claims, 11 Drawing Figures

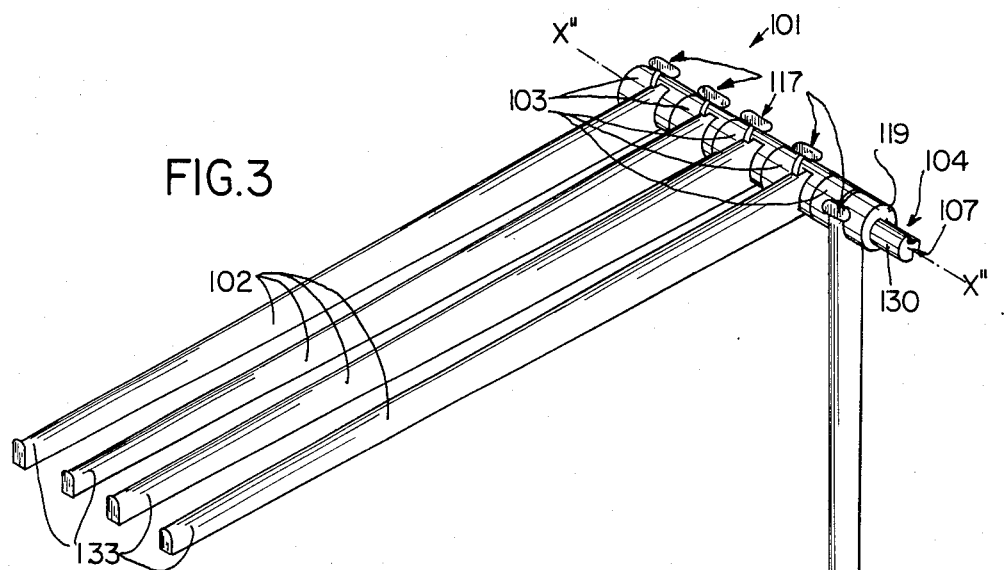
FIG. 3
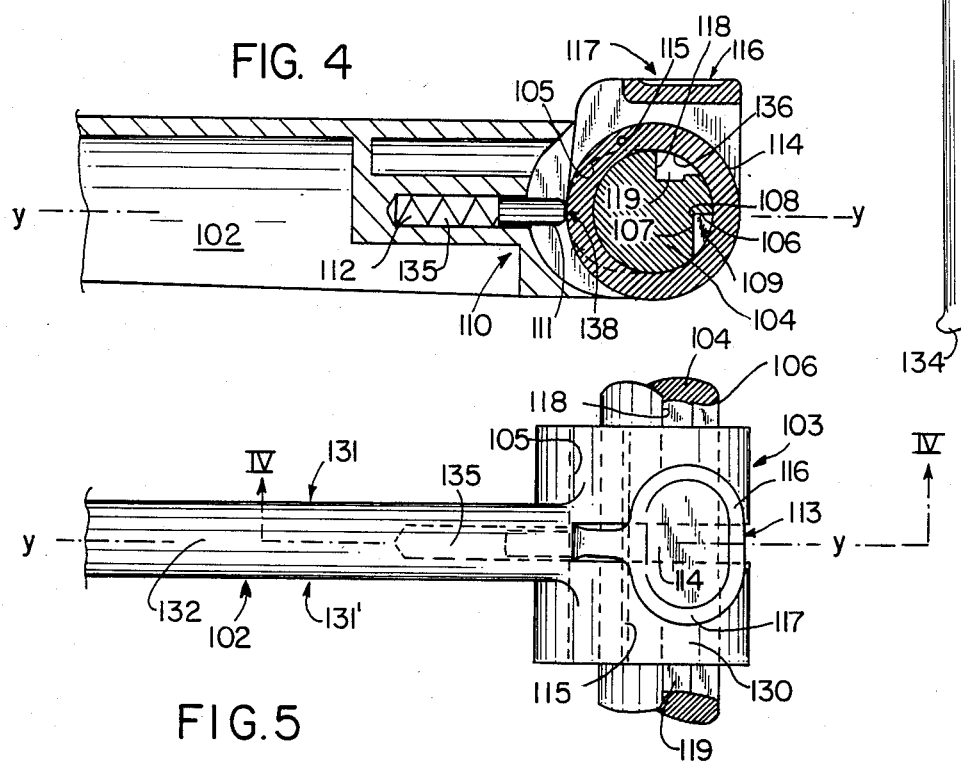
FIG. 4
FIG. 5

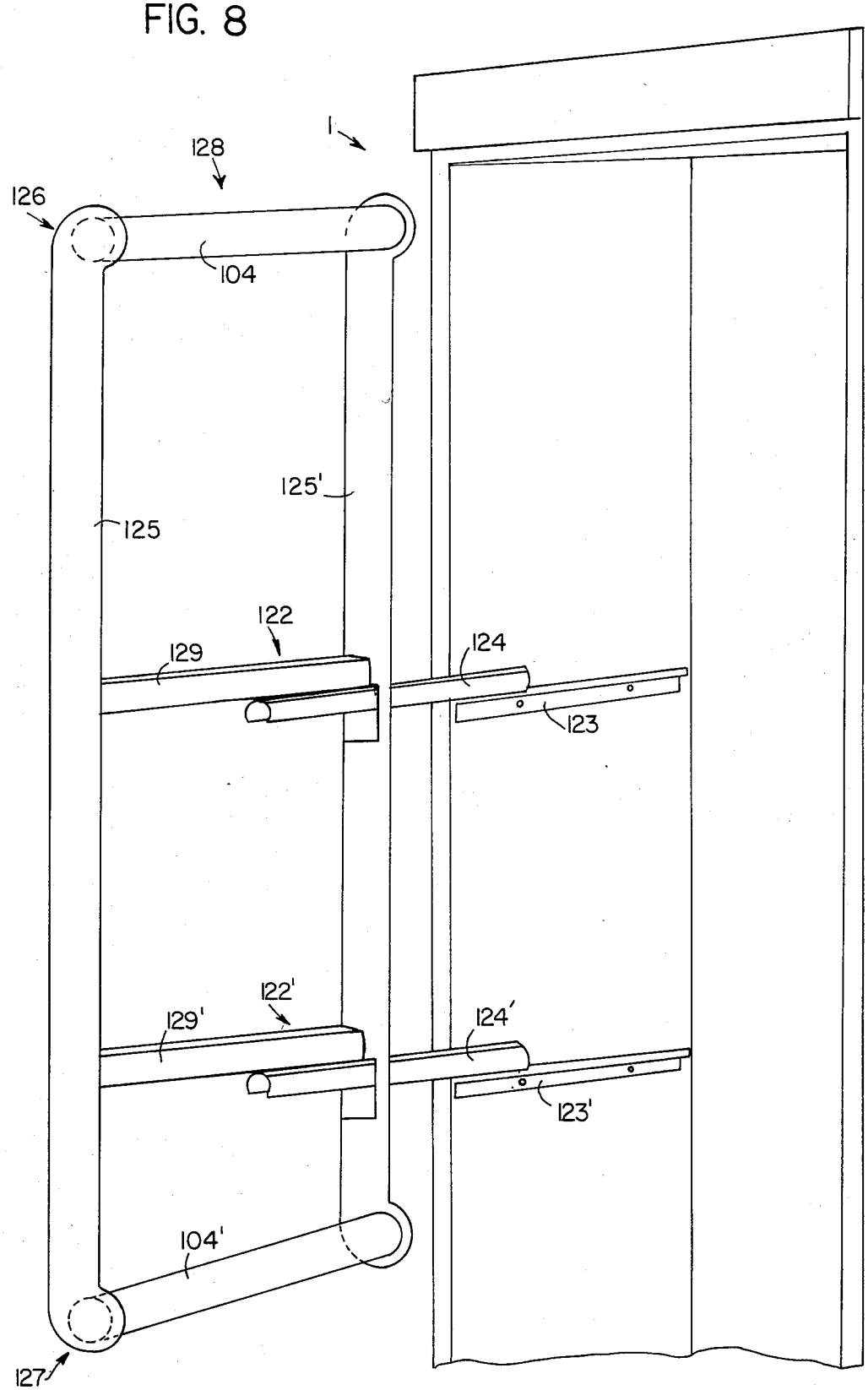

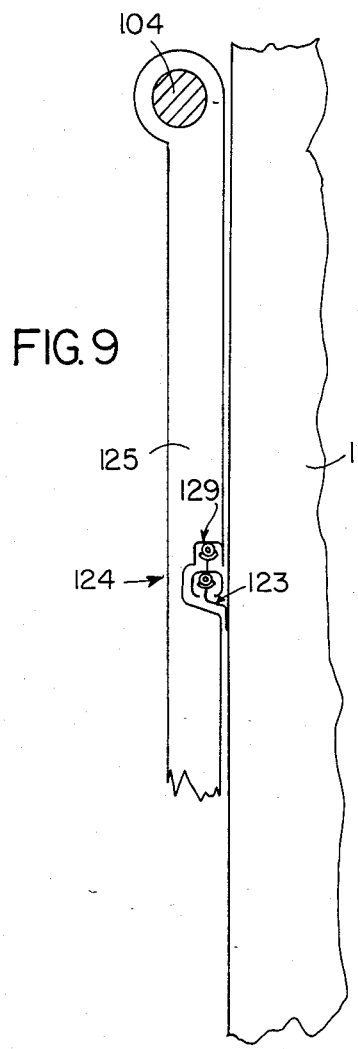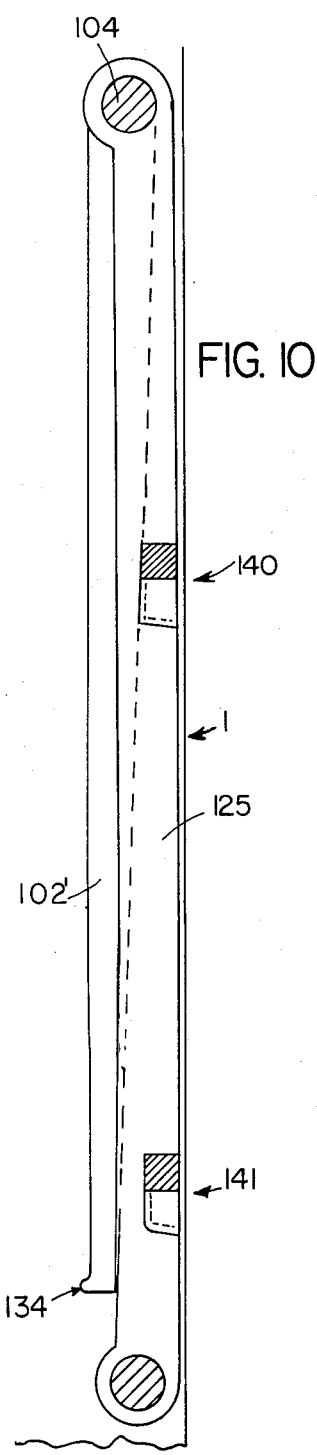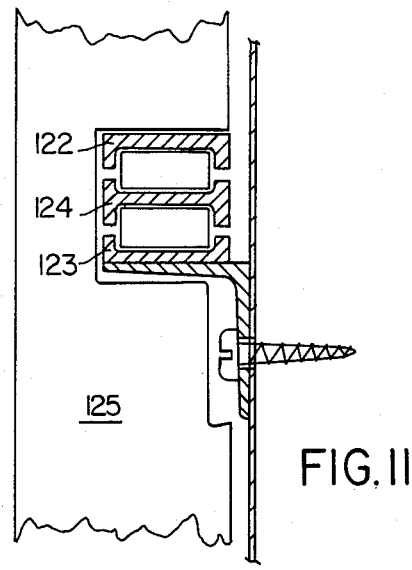

APPARATUS AND METHOD FOR DRYING AND STERILIZING FABRICS

The present invention relates to an apparatus and a method for drying and sterilizing fabrics.

As known, none of the most modern automatic washing machines is capable of boiling the laundry, as has been practice in former times, and thereby eliminating a major part of the bacteria. All of these washing machines, even when set to "boiling laundry", stop before the boiling process as such, i.e. prior to reaching a temperature of 100° C.

A major part of the laundry (pieces of cloth), primarily the constant by increasing portion of delicate mixed fiber fabrics, is washed in part at temperatures of as as low as 30°, 40°, 50° or 60° C., because these delicate fabrics cannot withstand higher temperatures under the mechanical strains imposed by the washing process, i.e. by the agitation.

For the same reason, none of the conventional rotary driers is capable of drying highly delicate fabrics, such as of pure wool or polyacryl. Further, these driers are specifically provided with a lower heating stage for drying at only from 50° to 60° C., for less delicate mixed fiber fabrics.

Accordingly, in spite of the fully automatic washing machines of most sophisticated design and of the electric rotary driers, no housewife is in a position to render her laundry to be in a biologically and hygienically properly clean state, namely also in a sterile state. As known, it is quite easy to become infected with mycosis of the feet or the most varied carriers or exciters in steam baths, swimming pools, hotels or on other occasions, while the germs or the like existing in the laundry cannot be eliminated even by a washing process or by most modern rotary drier treatment.

Therefore, in clinical applications and doctor's offices, all doctor's and nurse's coats or smocks, towels and other fabrics used in this field must be folded in inconvenient manner after the normal washing and drying process, and sterilized in a separate sterilization apparatus under well-known conditions at sterilizing temperatures of about or above 125° C.

Here, the synthetic fibers subjected to the sterilizing temperature in a folded state of the fabric tend to suffer from embrittlement and from fiber breaks at the positions of the folds when they are being unfolded. Another drawback is the expense of work for removing the dried clothes from the rotary drier, smoothening and folding them and packing them in layers into the sterilizer. Also, the clothes must be removed and unfolded after the sterilization.

An apparent proposal of improvement according to which the clothes are subjected to sterilization at elevated temperature in the rotary drier following the drying step, has been found to be impracticable because the fibers of delicate fabrics are upset, broken and thereby permanently damaged due to the intense motion or agitation processes and the resulting abrasion phenomena.

It is the object of the present invention to overcome the indicated restrictions and difficulties by providing an apparatus and a method by which it becomes possible to perform the drying and sterilizing operations of delicate synthetic fiber or mixed fiber fabrics without any problem and in easy manner, while preserving the fabrics to a maximum degree. The expense of work required herefor is to be reduced significantly. An apparatus contemplated to carry out these operations should be adapted to be operated in easy and uncomplicated manner, have a low energy consumption, and be adapted to be produced economically.

According to the invention, this object is solved in an apparatus for the drying and sterilizing of fabrics in that said apparatus comprises a drier cabinet including means for suspending therein fabric parts, and means for generating, distributing and especially circulating warm air for drying purposes and hot air for the sterilization of the fabric parts.

Advantageously, this structure allows saving a substantial portion of the formerly required work of clearing the drier, smoothening, folding and reloading the fabric into the sterilizer.

As both the drying operation and the sterilizing operation may be performed substantially without subjecting the fabric to motion (agitation), wrinkling or folding, most careful treatment of the fabric is achieved, especially when the sterilizing step is performed immediately after the drying in the drier cabinet.

This provides for optimum sterilizing results because the articles of cloth are prevented from being touched by human hand or contacted with unsterilized atmosphere in the period between the washed and the sterilized state. Besides, primary energy and, further, time and manpower are saved owing to the direct transition from the drying to the sterilizing operation. The smocks or coats and linen are kept smooth; besides, in contrast with the sterilization in a folded state, the clothes have the hot air flowing through them more evenly and therefore more effectively, so as to become sterilized in the shortest period of time possible.

In order to prevent the casing of the cabinet from becoming too hot, filtered fresh air aspirated through at least one intake port may be passed through both outer sides and also through the rear wall and the front door for cooling purposes. This structural extra expense is more than compensated for by the more intense heat exchange. In such case, the discharge of exhaust air is effected expediently through at least one opening in the bottom or in the top wall of the cabinet.

It is further contemplated that for the step-wise or incremental production of warm air for drying purposes and hot air for sterilizing purposes within a heater register through which air flows, such heater register is operated with unvaried energy input or unvaried heating capacity, respectively, and has air flowing there through at different rates of flow. This is achieved, for example, in that for the sterilization the aspiration of fresh air to (be admixed to) the circulating hot air, and/or the discharge of exhaust air from the circulating hot air is/are at least substantially restricted. Advantageously, this measure both saves energy and prevents the entry of non-sterilized ambient air.

Another possibility resides in that the blower includes means for adjusting the rate of air supply, preferably in at least two steps. Reducing the rate of air supply allows obtaining an extended residence time of the air while flowing through the heater register, and thus improved heat exchange, and, consequently, an increase in temperature of the circulated air. In view of the fact that in the sterilizing process, unlike the drying process, the quantity of the circulated hot air may be greatly reduced anyhow, the reduction of the rate of feed of the blower in the production of hot air constitutes and ingeniously simple measure which, besides, may be realized at a minimum of expense of technical means.

Preferably, the drier cabinet is designed so that the drying may be performed at warm air temperatures of below 100° C., and sterilization may take place at hot air temperatures in the range of between 120° and 145° C., preferably between 125° and 135° C. When performing the sterilization in the drier cabinet with the articles being in a hanging or suspended state, a sterilizing temperature of the upper practicable limit may be used with advantage, because owing to the careful treatment the fabrics are not subjected to any further undue strains, such as agitation, wrinkling, etc., aside from the temperature action.

In extreme instances, however, the measure may be used by which the hot air has added thereto as bactericidal substances in the form of glases, vapors or aerosols, for example, halogenated hydrocarbons, such as carbon tetrachloride, trichloroethylene and the like. It is further possible to admix to the hot air, chlorine, preferably by spraying chlorinated water into the hot air.

The measure of auxiliarily using bactericidal substances is advisable when, due to a maximum delicate nature of the fabric (textile) fibers, it would not be expedient to perform the sterilization at the requisite temperature limit of, for example, 125° C. Accordingly, the addition of bactericidal substances manner permits to carry out an effective sterilization at a low temperature level while providing for as careful as possible a treatment of the fabric.

Advantageously the means for suspending fabric parts within the drier cabinet comprise bars adapted to swing about a horizontal axis and releasably arrested or locked in an approximately horizontal position, wherein a hinge pin forming the horizontal pivot axis has a circular profile (cross-section) including a notch defining an engagement surface in the side opposite from a horizontally positioned bar, and the bore is configured, in profile, as an elongated or oval hole having a profile axis co-extending with the bar axis (y—y), and having a detent protruding into the elongated hole at the side opposite from the bar and defining a counter engagement or arresting surface which extends in parallel with the axis (y—y), with the notch in cooperation with the detent defining lock or latch elements of a lock means, and that a reset element keeping the lock or latch elements in the engaged position is provided in the head portion at the side opposite from the lock or latch elements of the elongated hole.

This solution results in the most simple configuration conceivable of the pivotable rods or bars for suspending the pieces of fabric within the drier cabinet according to the invention. Here, the provision of the engagement (arresting) surface and the counter engagement (arresting) surface profides for a perfectly regular horizontal position of the bar grid formed by swinging the bars upwards, particularly also for the reason that the resilient reset element, e.g. a spring-loaded pressure bolt or detent, urges the lock or latch elements into positive angagement. Another advantage with respect to operability results from the fact that it is no longer necessary for the heat portion to be raised for unlocking; rather, a pressure exerted by hand from the end of the bar toward the head portion is sufficient to unlock the latch.

According to another essential embodiment of the invention, for overcoming the resetting force of the reset element and, thus, for releasing the lock means, a shift lever is slid with a circular opening onto the hinge pin in the recess of the yoke, the shift lever being pivoted to the yoke in a joint positioned centrally above the elongated hole, and formed with a manually operable actuating cam protruding above the yoke to the rear upper side. This cam is preferably formed with a cup-shaped enlargement to form an operating key, and clearly marked by a color marking in a signal color, preferably in red.

This results in a highly uncomplicated operability readily understandable to everybody without special instruction, thereby to virtually prevent misoperation or damage. Of special advantage is the dual operability during swinging or folding the bars down, which results from the fact that unlocking may be effected either by pressure applied to the free end of the bar, or by operating the actuating key by finger pressure.

Another advantageous embodiment resides in that the hinge pin includes at the upper side of its profile a second notch being displaced from the notch by 90° and defining a vertical engagement surface, which second notch defines together with the counter engagement surface of the detent a locking means preventing further pivoting (of the bar) beyond the vertical position when the bar is pivoted to a vertical position.

This constitutes an improvement over prior constructions in which the bar in the course of swinging down, when inattentively operated, might strike agains the cabinet wall and thereby cause at least substantial noise or even damage.

In order to facilitate as far as possible the suspending of the fabrics from the bars, it is further contemplated that the hinge pin equipped with bars, or an assembly of a plurality of hinge pins, are adapted to be shifted separately or commonly from a position within the cabinet to a position outside of the cabinet, across one or more telescoping rails. Thus, the entire bar assembly may be drawn out from the cabinet and freely hung with pieces of cloth.

A further improvement of these structures is achieved in that at least two hinge pins, equipped with bars and joined to telescoping bars through vertical struts, are formed as assembly group or module adapted to be prefabricated for installation in the drier cabinet.

By connecting the superposed hinge pins or the bar assembly to form a rigid frame, both the stability of the bar assemblies adapted to be drawn out from the cabinet is substantially improved, and the manufacturing and assembly work is greatly facilitated and thereby rendered more economical and efficient.

Preferably, the hinge pins are extruded light-metal hollow profiles (sections), and the bars comprise U-sections formed from fiberglass-reinforced, temperature resistant plastics material and having depending legs and a semi-circular back (upper side), which bars taper toward the free end, similar to beams of identical bending strength, and are provided with a nose or lug on the free end thereof. Likewise, the shift gate may be preferably a plastic molded part.

In a particularly advantageous embodiment, the drier cabinet described above is operated in accordance with a method wherein the air for drying and sterilizing is, in part, passed in circulation.

The invention is described below in a preferred embodiment with reference to drawings, with the drawings showing further advantageous details of the invention.

In detail, in the drawings:

FIG. 1 shwos a drier cabinet according to the invention for drying and sterilizing fabrics;

FIG. 3 is a perspective view of a device for suspending pieces of fabric within the drier cabinet, including a hinge pin having a series of pivotally slid-on laundry rods or bars, with four bars being in a horizontal position to define a holding grid, and one bar assuming a downwardly swung vertical position;

FIG. 4 is a sectional view of a hinge assembly;

FIG. 5 is a plan view of a hinge assembly;

FIG. 8 is a perspective view of a frame including frame struts and a pair of hinge pins disposed one below the other, illustrated without the bars for reasons of clarity, and drawn out from a cabinet on telescoping rails;

FIG. 9 is a side elevational view of a frame strut mounted on telescoping rails;

FIG. 10 is a side elevational view of a frame strut according to FIG. 9 with laundry bars folded down; and FIG. 11 is a sectional view of a telescoping rail guide means, approximately to natural scale.

Figure 1:
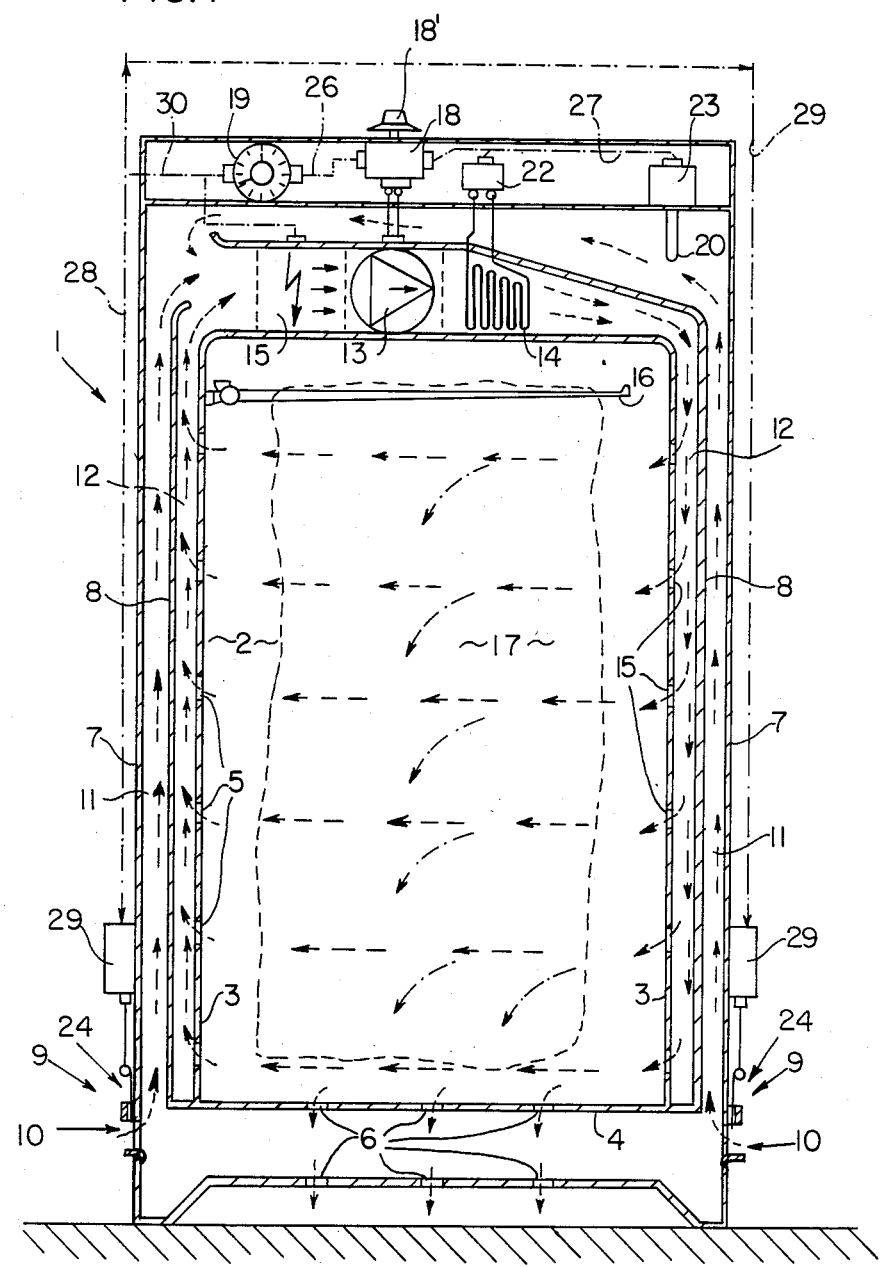

As illustrated in FIG. 1, the drier cabinet 1 includes in inner space 2 adapted to receive pieces of cloth in a hanging state. The drier cabinet is provided with hanger devices 16 from which pieces of cloth 17 may be hung up. Such clothes suspensions or holders for the drier cabinet have come to be known, for example, from the prior German Patent No. 21 49 873 or from the prior German patent application No. P 27 05 116, respectively, to which explicit reference is herewith made. The inner space 2 of the drier cabinet 1 is enclosed by walls 3, 4 which, in turn, are provided with air circulatin holes 5. Air outlet ports 6 are provided in the bottom wall 4. Owing to the countercurrent air conduction, as indicated by arrows in the Figure, in which the air flows evenly at every level of the inner space 2, the clothes 17 suspended therein are uniformly contracted and aerated by the air flow. The drier cabinet comprises an outer casing 7 of sheet metal or plastic. Heat exchanger walls 8 are provided between this casing and the inner walls 3. Fresh air inlet ports 10 are provided in the lower portion 9 of the outer casing 7. From these inlet ports, fresh air flows into the system of the drier cabinet 1 through fresh air ducts 11 which are defined between the casing 7 and one of the heat exchanger walls 8 each. System air flows in parallel flow (left side of the cabinet) or in countercurrent flow (right side of the cabinet) relative thereto from the interior of the cabinet through circulatin air ducts 12. A blower or fan 13 is provided in the upper portion of the drier cabinet 1, and this blower has the heater register 14 disposed downstream thereof. In the embodiment of the invention, the blower 13 is provided with a device for setting different speeds of rotation, for example, with a pole-changeable asynchronous motor for two ranges of speed of rotation. By means of the multiple-contact or stepping switch 18, the desired range of speed of rotation may be set manually by means of the switch knob 18'. On the other hand, the stepping switch 18 is connected through control line 26 to a timer mechanism 19 which permits selecting in digital manner or with the use of program cards a program of operation according to which, for example, loaded clothes 17 in their moist state after washing may be subjected initially to a drying process at warm air temperatures, and, upon termination of the drying process, to a sterilizing process at sterilization temperatures. Normally, warm air temperatures for drying may be chosen to be below 100° C., while sterilization requires a temperature of about 125° C. In order to provide warm or hot air in the first instance, the blower 13 rotates at a higher stage of speed of rotation, whereby a greater volume of air of a lower temperature is circulated. Upon initiation of the sterilization process, the blower 13 is switched to a lower speed of rotation, whereby a smaller volume of air of a higher temperature is fed. In order to prevent an upper temperature limit from being exceeded, the drier cabinet 1 is additionally equipped with an overheat (protection) switch 23. The latter includes a temperature sensor 20 for sensing the temperature of a gas (air) flow at an expedient position of the flow ducts such as, for example, within the return duct 11. This overheat (protection) switch 23 is connected to the switching relay 22 via a control line 27. This structure results in a most simple function of the overheat protection means in the go-stop-go-stop operation, whereby the heater register 14 is turned off each time the permissible upper temperature limit is reached or exceeded, and turned on again when the temperature has dropped to a permissible temperature level.

In the sterilizing operation, especially for delicate synthetic fiber fabrics, the sterilizing temperature is expediently maintained exactly within an allowable range of, for example, between 125° and 130° C. In this operation, it is advisable to greatly restrict the supply of fresh air which is desirable during the drying cycle, and at the same time also to greatly reduce the volume of system air flowing in circulation. To this end, the drier cabinet 1 designed for carrying out the sterilizing process includes shut-off dampers 24 at the air intake ports 10, as auxiliary means.

In the illustrated embodiment, these dampers are adapted to be operated automatically with the aid of electromechanical actuation means 29, preferably embodied as lifting magnets or solenoids. Control is effected by the program of the timer mechanism 19 through control lines 28. In the illustrated embodiment, these lines are shown in a purely schematic form and, in practice, self-evidently installed within the drier cabinet in the normal safe and concealed manner.

The mode of functioning of the drier cabinet 1 during the drying and sterilization of pieces of cloth 17 suspended therein, as far as it is not evident already from the preceding specification, may be explained as follows:

After clothes 17 to be dried and sterilized have been loaded into the drier cabinet 1, the latter is closed, and a corresponding program is set or selected by means of the timer mechanism 19, whereupon first the drying operation is initiated, carried out and terminated, while the sterilizing process is performed immediately thereupon. Here, drying is effected with a given drying time (period) and drying temperature as well as (drying) air volume, in the conventional manner. At the end of the drying operation, the speed of rotation of the blower 13 is reduced by means of the pole-changeable motor in accordance with a corresponding command from the program, through the stepping switch 18. Accordingly, a smaller volume of air of higher temperature is fed through the heater register 14 which is operated with unvaried energy input. Exceeding of the upper permissible temperature limit is prevented from occuring by the overheat switch 23 including the temperature sensor 20. At the same time, a corresponding control pulse of the program, supplied via the control lines 28, acts to greatly restrict or even prevent air inflow through the air intake ports 10 with the aid of the shut-off dampers 24.

In order to further activate the now circulating hot sterilizing air, an additional bactericidal agent may be admixed to the hot air flow. In the embodiment shown, the drier cabinet 1 includes to this end an ozone generating chamber 15 which is likewise controlled by the program of the timer mechanism 19 via a control line 30. Furthermore, the drier cabinet may be provided with means for introducing a desired bactericidal agent, which means is not illustrated in the drawing, however.

Of course, the provision of the ozone generating chamber is not mandatory. Further, manually operable shut-off dampers may be provided at the air intake ports 10 and also at the air outlet or exhaust ports 6, instead of the electromechanically controlled shut-off dampers 24.

According to the invention, for use as a sterilizing apparatus the drier cabinet requires only a higher expenditure of technical means, compared to its previous conventional use as an exclusive drier cabinet. Consequently, the object as outlined above is solved in an ideal manner by the apparatus described.

For the suspension of clothes, such as smocks or blouses, these articles may be hung on hangers having widened hooks such that the hangers are prevented from rotating relative to the bars.

The air guide system and the arrangement of the operating elements may be designed, even in the case of a small-size wall mounted cabinet, such that this cabinet, in case of need, may be mounted above the heat or foot end of a bathing tub.

Furthermore, the particular advantage of the cabinet resides in the fact that the risk of fire is excluded therein in spite of the high temperatures used, because flint does not deposit anywhere in the cabinet, and drying can be performed even without heating.

Figure 2:
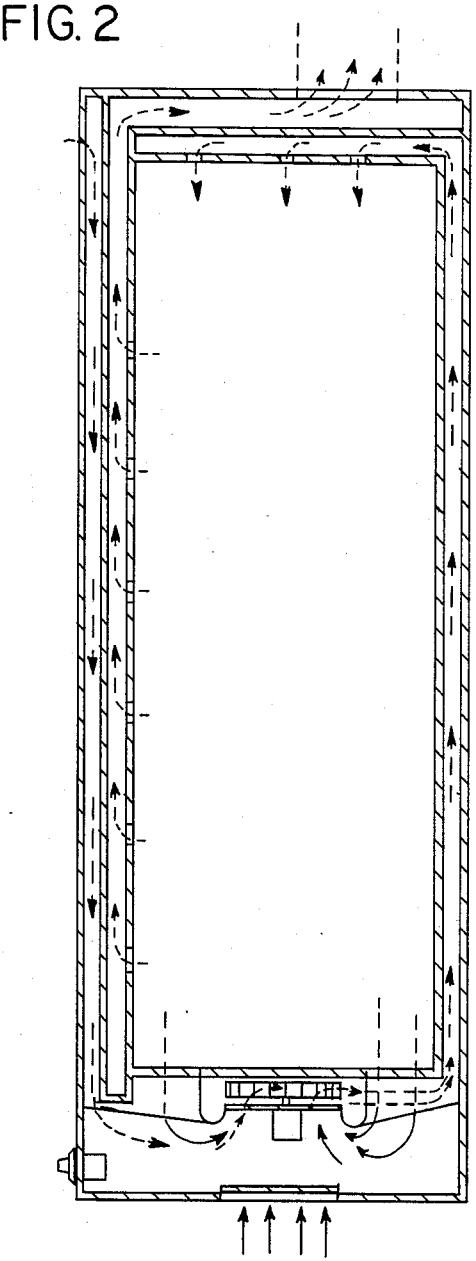
FIG. 2 shows an embodiment of the drier cabinet according to the invention with modified air guiding means.

In order to minimize a heat loss during the drying and sterilizing operation, and thus to minimize the thermal load to the environments of the cabinet, according to FIG. 2 not only the sidewalls, but also the rear wall, the door, the top wall and the bottom wall may be formed of double sheet and include external cold air guide means. Also, the walls may be formed optionally as insulating walls.

More particularly, in such case, the cold air is drawn in or aspirated at the cabinet bottom to flow upwards within one wall of the cabinet, pass through the top wall and flow down within the opposite wall of the cabinet, to be exhausted at the upper side after having passed through the drying compartment.

Interiorly, the drier cabinet according to the invention, as appears from FIG. 3, includes a hinge assembly 101 comprising rods or bars 102, 102' for suspending there from pieces of cloth and the like. In the illustrated structure, the bars 102 are shown in the horizontal position ready to receive the pieces of cloth, whereas the bar 102' is folded down to assume a vertical position. In the hinge assembly 101, the bars 102, 102' are formed at the side adjacent the hinge, with a hub-shaped head portion 103 extending transversely of the bar axis x—x. The head portions are provided with bores 130 by which they are mounted for pivoting movement about a horizontally extending hinge pin 104, and set either to project in a horizontal position adapted to be secured by lock or latch elements, or to be folded down to the vertical position upon release of the lock. The hinge pin 104 has a circular profile with a notch 107 defining a horizontal engagement (or arresting) surface 106 and extending in parallel with its axis x—x at the side opposite from a horizontally extending bar 102. The bore 130 formed in the head portion is formed, in profile or cross-section, as an elongated or oval hole 105 having a profile axis that coincides with the bar axis y—y. At the side opposite from the bar, a detent 109 protrudes into the elongated hole 105, which detent defines a counter engagement (or arresting) surface 108 extending in parallel with the bar axis y—y.

In the horizontal position of a bar 102, the detent 109 engages the notch 107, with the detent and the notch defining engagement or arresting elements of a lock means. In this situation in which the parts engage with each other to cooperate in defining the lock means, the head portion 103 and the hinge pin 104 are retained by the action of the resilient reset element 110. Here, the engagement surface 106 and the counter engagement surface 108 are each formed such that these surfaces contact each other with planar faces when engaged with each other.

As is further apparent from the illustration of FIGS. 4 and 5, the head portion 103 is formed with a central recess 113 to constitute a yoke. In the bottom of the recess 113, a bore 135 is formed to extend in the direction of axis y—y, which bore receives the reset element 110 in the form of a thrust bolt 111 biased by a compression spring 112.

Figure 6:
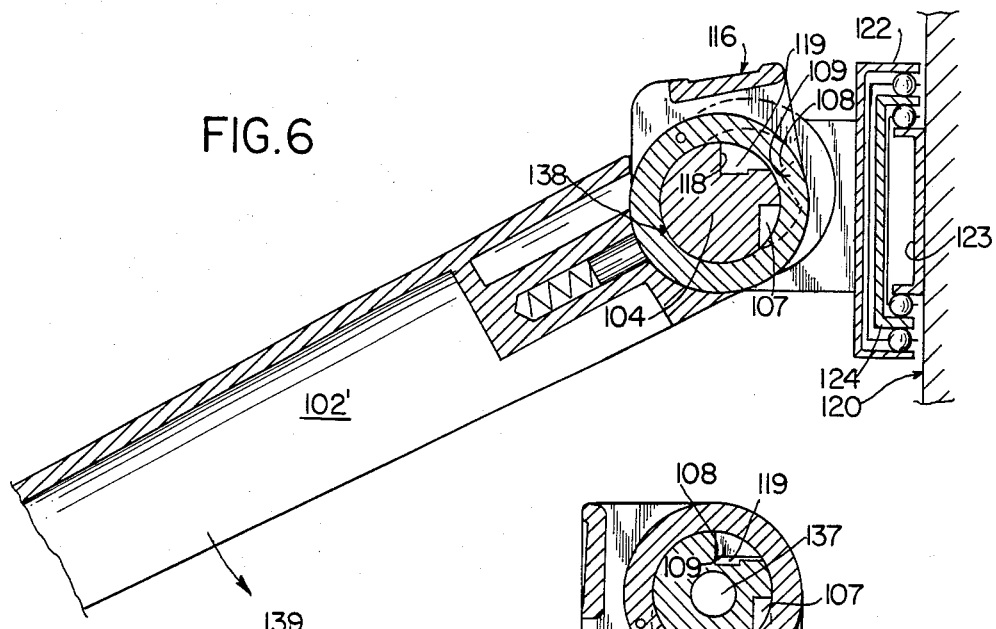
FIG. 6 shows a hinge assembly in the unlocked position, in longitudinal section along plane IV—IV of FIG. 5.

To overcome the resetting force of the reset element 110 and, thus, to release the lock, a shift lever 114 is positioned in the recess 113 of the yoke, which is slid on the hinge pin 104 with a circular opening 136 and pivotally connected to the yoke 104 through a joint 115 disposed centrally above the elongated hole 105. The shift lever 114 is formed at the upper rear and with a manually operable actuating cam 116 projecting above the yoke. This cam is provided with a cup-shaped enlargement 117 to form an operating key. Upon despressing this key by finger pressure, the key pivots about the joint 115 against the resetting force of the reset element 110, thereby to shift the hinge pin 104 relative to the bar 102 or the head portion 103 with the degree of freedom defined by the elongated hole 105, and into abutment with the bar-side end 138 of the elongated hole 105. This position of the hinge pin 104 relative to the elongated (oval) hole 105 is clearly shown in the illustration of FIG. 6. By this relative movement, the engagement surface 106 is released from the engagement with the counter engagement surface 108, and the bar 102 may be swung or folded down to the vertical position, as indicated by the arrow 139 in FIG. 6.

As can be seen from FIGS. 4 to 7, the hinge pin 104 is provided with a second notch 119 which is displaced by 90° C. from the first notch 107. According to FIG. 7, the detent 109 engages this notch in the vertical position, whereby the counter engagement surface 108 is brought into surface contact with the vertical engagement or arresting surface 118 of the second notch 119. Accordingly, in this state the bar 102 is locked in its vertical position, thereby to positively prevent overtravel beyond the vertical position and, thus, striking of the bars 102 against the inner wall of the cabinet 1.

As can be seen especially from FIGS. 3 and 5, the notches 107 and 119 are formed to extend in parallel with each other and with the axis x—x of the hinge pin 104.

Furthermore, easy operation is particularly facilitated by the fact that the operating cam 116 of the shift lever 114 is provided with a colored marking in a signal color, preferably in red. Accordingly, the "push button" which must be actuated for folding down a bar 102, 102' immediately strikes the eyes of even a most inexperienced person.

Figure 7:
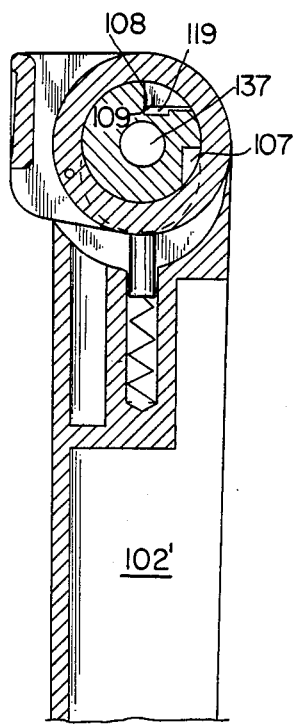
FIG. 7 shows the hinge assembly according to FIG. 6 in the folded-down state, likewise in section along plane IV—IV.

In order to facilitate hanging of the pieces of cloth from the bars 102, the hinge pin 104 provided with the bars 102, 102' is mounted in a telescoping rail guide. Here, the hinge pin 104 is fixedly mounted to the telescoping rail 122, and the wall of the cabinet 1 is fixedly connected to the telescoping rail 123. An interposed telescoping rail 124 being slidable relative to the other two telescoping rails provides for almost friction-free movement in a horizontal direction in parallel with the x—x axis until the hinge assembly 101 is drawn out fully from the interior of the cabinet 1. According to FIG. 8, a further improvement is compared to this structure is obtained in that at least two hinge pins 104, 104' form together with vertical struts 125, 125' an integrally rigid rectangular frame 128 In the illustration of FIG. 8, the bars 102, 102' have been omitted for reasons of clarity, but these bars, of course, are mounted on the hinge pins 104, 104' in the installed and assembled state. These hinge pins are each securely connected to the upper ends 126 and the lower ends 127 of the vertical struts 125, 125'. According to a further proposed embodiment, such a connection may be realized expediently when the hinge pins 104—as shown in FIG. 7—are formed as profiled extruded light-metal hollow sections. In this instance, a (not illustrated) tie rod or stay may be inserted through the opening 137 of the profile and threadingly joined to the ends 126, 127 of the vertical struts 125, 125' under a pretension. Further, the frame 128 is reinforced by cross-bars 129, 129'. These latter elements, in the example shown, are formed as telescoping rails 122, while telescoping rails 123, 123' are fixedly screwed in the interior of the cabinet 1. Joining of these telescoping rails is effected by means of telescoping intermediate rails 124, 124' in a manner being known per se. The assembly of the hinge pins 104, 104' integrated into the rigid frame 128 including the vertical struts 125, 125' constitutes, as a module, a prefabricated assembly group for installation into the drier cabinet 1. This provides for significant savings in production time and for a separate line productability of this assembly group. On the one hand, this permits to reduce production cost; on the other hand, the varying requirement with respect to the equipment of a drier cabinet with an installed bar structure can be met more flexibly, finally, the pull-out installation group greatly facilitates the necessary manipulations by the user.

The placement of a vertical strut 125 on telescoping rails 122 to 124 is shown in FIG. 9. In this structure, a cross-bar 129 constitutes the uppermost telescoping rail 122, and an S-shaped angled section defines the lower telescoping rail 123 mounted in the cabinet 1, with a telescoping intermediate rail 124 arranged therebetween to be movable.

One of the great number of variants for realizing such a known per se telescoping rail assembly is shown on an enlarged scale in FIG. 11.

Finally, FIG. 10 shows in a purely schematical illustration in connection with telescoping guide means 140, 141 a vertical strut 125 in side elevational view, with the bars 102' folded down to the vertical position.

Evidently, the hinge assembly according to the invention combines optimum functioning and maximum comfort of operation with an ingeniously simple construction and, therefore, the potential for highly efficient manufacture, while avoiding the heretofore existing problems and drawbacks.

A particularly great length of the bars which provides for a corresponding length for suspending articles, results from the positioning of the telescoping rails 122, 124 and 123 one above the other. This necessitates that the cabinet-side vertical strut 125' is provided with a cutout to permit the rails 122 and 124 to pass therethrough when the bars are retracted into the inner space of the cabinet.

I claim:

1. Apparatus for drying and sterilizing fabrics comprising:
   a drier cabinet having walls;
   means for suspending fabric parts in said cabinet; and
   means for generating, distributing and circulating first warm air in said cabinet for drying purposes and thereafter hot air for the sterilization of the fabric parts;
   means to cool said cabinet walls by causing fresh air to flow along at least a portion of the interior of said walls of said drier cabinet to cool same comprising distributing ducts in at least a portion of said walls and including at least one fresh air inlet port in at least one of said walls, said distributing ducts directing said fresh air to said means for generating, distributing and circulating first warm air, and at least one exhaust air outlet port in at least one of said walls.

2. The apparatus according to claim 1, in which said means for circulating air comprises distributing ducts in at least a portion of said walls and includes at least one fresh air inlet port and at least one exhaust air outlet port.

3. Apparatus according to claim 1, in which cold air is aspirated in a portion of said walls and passed behind said walls through passages for cooling the outer surfaces of said drier cabinet, to an opposite portion of said cabinet.

4. Apparatus according to claim 2, in which at least one of said two ports includes a controllable restriction element.

5. Apparatus according to claim 1, which produces warm air of a temperature below 100° C. for the drying operation, and hot air in a temperature range between 120° and 145° C. for the sterilizing operation.

6. Apparatus according to claim 1, in which said drier cabinet includes means for introducing a bactericidal agent.

7. Apparatus for drying and sterilizing fabrics comprising a drier cabinet, means for suspending fabric parts in said cabinet, and means for generating, distributing and circulating warm air for drying purposes and hot air for the sterilization of the fabric parts, and said means for suspending fabric parts in said drier cabinet comprising bars individually having head portions and adapted to swing about a horizontal axis and releasably locked in an approximately horizontal position, said suspending means including a hinge pin forming a horizontal pivot axis and having a circular cross-sectional profile including a notch defining an engagement surface in the side opposite from each of said bars in a horizontal position, and each bar having a bore configured, in profile, as an elongated hole having a profile axis co-extending with the bar axis, and said head portion of each bar having a detent protruding into said elongated hole of each bore at the side opposite from the bar and defining a counter engagement surface which extends in parallel with the bar axis, said hing pin having a notch and said each bar head portion having a detent comprising lock means having lock elements, and said each bar head portion having at the side opposite from the lock elements a reset element keeping the lock elements in the engaged position.

8. Apparatus according to claim 7, in which each head portion has a recess to form a yoke and which includes for each head portion a shift lever with a circular opening and disposed on said hinge pin in said recess for overcoming the resetting force of said reset element and, thus, for releasing said lock means, said shift lever being pivoted to said yoke centrally above said elongated hole and said shift lever having a manually operable actuating cam protruding above said yoke to the upper rear side thereof.

9. The apparatus according to claim 8, in which said hinge pin includes at the upper side of its profile a second notch displaced from the first-mentioned notch by 90° and defining a vertical engagement surface, which second notch comprises together with said counter engagement surface of each detent locking means preventing further pivoting of said each bar beyond the vertical position when said each bar is pivoted to a vertical position.

10. Apparatus according to claim 7, which includes a plurality of hinge pins adapted to be shifted from a position within the cabinet to a position outside the cabinet.

* * * * *